US008465559B2

(12) United States Patent
Guay et al.

(10) Patent No.: US 8,465,559 B2
(45) Date of Patent: Jun. 18, 2013

(54) LIGNIN-SOLVENT FUEL AND METHOD AND APPARATUS FOR MAKING SAME

(75) Inventors: Donald F. Guay, Stevens Point, WI (US); Eric L. Singsaas, Stevens Point, WI (US)

(73) Assignee: Wisys Technology Foundation, Inc., Madison, WI (US)

( * ) Notice: Subject to any disclaimer, the term of this patent is extended or adjusted under 35 U.S.C. 154(b) by 0 days.

(21) Appl. No.: 13/540,278

(22) Filed: Jul. 2, 2012

(65) Prior Publication Data

US 2012/0329146 A1 Dec. 27, 2012

Related U.S. Application Data

(62) Division of application No. 12/332,019, filed on Dec. 10, 2008, now Pat. No. 8,211,189.

(60) Provisional application No. 61/012,650, filed on Dec. 10, 2007.

(51) Int. Cl.
*C10L 1/00* (2006.01)

(52) U.S. Cl.
USPC .................................. 44/307; 127/1; 127/32

(58) Field of Classification Search
USPC ........................................... 44/307; 127/1, 32
See application file for complete search history.

(56) References Cited

U.S. PATENT DOCUMENTS

| | | | |
|---|---|---|---|
| 6,465,609 B2 * | 10/2002 | Ko et al. ........................ | 528/490 |
| 2008/0032344 A1 * | 2/2008 | Fallavollita ..................... | 435/72 |
| 2008/0299628 A1 * | 12/2008 | Hallberg et al. ............... | 435/139 |
| 2011/0097769 A1 * | 4/2011 | Del Cardayre et al. ........ | 435/134 |

* cited by examiner

*Primary Examiner* — Jim Goloboy
(74) *Attorney, Agent, or Firm* — Boyle Fredrickson, S.C.

(57) ABSTRACT

The present invention is a process and apparatus for forming various bio-products from cellulosic plant material. The plant material is subjected to a pulping step in which lignin is extracted from the material by an aqueous lignin solvent to form a lignin-solvent mixture and purified cellulose. The lignin-solvent mixture can be separated from the water to form a high energy density fuel that can be used independently or combined with biodiesel. The purified cellulose can be used in conventional processes, e.g., paper making, or can be converted to fermentable sugars with a cellulase enzyme to produce other bio-products depending on the operating conditions of the fermenter. The bio-products produced by the fermenter can include the solvent that may be recycled for use in extracting the lignin.

7 Claims, 4 Drawing Sheets

LIGNIN-SOLVENT FUEL AND METHOD AND APPARATUS FOR MAKING SAME

CROSS-REFERENCE TO RELATED APPLICATIONS

This application claims priority as a divisional of U.S. Ser. No. 12/332,019, filed on Dec. 10, 2008 and issued as U.S. Pat. No. 8,211,189, on Jul. 3, 2012, which in turn claims priority from U.S. Provisional Application Ser. No. 61/012,650, filed on Dec. 10, 2007, the entirety of which are each expressly incorporated by reference herein.

FIELD OF THE INVENTION

The present invention relates to liquid biofuels and in particular to a process generating liquid biofuels from plant fiber.

BACKGROUND OF THE INVENTION

The development of fuels from renewable agricultural sources is currently and will likely continue to be important in meeting future energy demands and reducing the production of greenhouse gas emissions from fossil carbon sources. Current "biofuels" under development include "biodiesel" derived from vegetable oil and ethanol fermented from sucrose obtained from plants such as corn and sugar cane.

A potentially plentiful source of biomass for the creation of biofuels is plant fiber found in agricultural residues such as corn stover and bagasse or crops grown specifically for fuel production including hardwood and softwood trees, among other sources. More specifically, the cellulose polysaccharides found in the plant fiber can be broken down into simple sugars and subsequently fermented to produce ethanol.

In order to promote the effect of cellulase enzymes in "saccharification" of cellulose in order to place the cellulose polysaccharides in condition for being broken down into the simple sugars for fermentation, it is necessary to remove the cellulose from its protective lignin. A number of techniques exist for mechanically removing the lignin and exposing the cellulose, including for example steam explosion techniques. In addition, the Kraft or sulfite pulping process removes lignin from the cellulose fibers by treatment with sodium hydroxide, sodium sulfide, or salts of sulfuric acid as a predicate to papermaking. In conventional papermaking, after the lignin is removed from the cellulose, the lignin is burned in boilers to recover the inorganic pulping chemicals used to remove the lignin and provide energy to be utilized for operating the pulping process.

In an alternative process to the Kraft or sulfite processes, ethanol may be used in an aqueous solvent extraction process to dissolve the lignin from the plant fiber, thereby removing it from the cellulose. This solvent extraction of lignin may be preceded by a hydrolytic cleavage of the lignin into smaller molecular weight fragments to improve its solubility. In this "organosolv" process, the extracted lignin, uncontaminated by the harsh pulping chemicals utilized in the Kraft or sulfite processes, maybe broken down into various products, such as the biofuel ethanol, which can be sold for a variety of commercial purposes, or used as a source of ethanol for the organosolv process, as illustrated in FIG. 4. Such organosolv processes include the Alcell® process described in U.S. Pat. No. 4,764,596, incorporated by reference herein, and improvements of which are commercially available from Lignol Innovations Limited of Canada.

However, when utilizing the organosolv process, after removal of the cellulose from the lignin, the lignin and the aqueous ethanol solvent are separated from one another in order to be able to recycle the ethanol as the solvent for the organosolv process, and to enable the remaining components to be used to form the other products via various separation processes, as illustrated in FIG. 4. It is necessary to employ a number of other devices and apparatuses to perform these separation processes, many of which require a significant amount of energy in order to perform the separation. In particular, because the solvent used to separate the lignin in the organosolv process is ethanol, which is very soluble in water, a highly energy-intensive distillation process is required to separate the ethanol to recycle the ethanol for use as the solvent in the organsolv process, or to use the ethanol as a biofuel.

As a result, it is desirable to develop a process for separating lignin from cellulose that is applicable to various sources of biomass material, which is less energy-intensive than prior lignin separation processes and that produces a high energy density biofuel.

SUMMARY OF THE INVENTION

According to one aspect of the present invention, a process for forming a biofuel is provided that utilizes an extraction or organosolv process with a water insoluble, or hydrophobic solvent to produce a biofuel formed of lignin and a solvent. A suitable biomass material is added to the solvent in the organosolv process to remove the lignin from the cellulose in the biomass. Once the lignin has been removed from the cellulose in this process, the cellulose can be separated from the lignin or other uses, and the lignin and solvent mixture is passed through a separator in order to remove excess water from the lignin/solvent biofuel.

According to another aspect of the present invention, the organosolv process can also be utilized to remove hemicellulose present in the biomass material from the lignin and the cellulose. The organosolv process utilized with the non-water soluble or non-polar solvent on the biomass produces three fractions, namely a solid cellulose fraction, an aqueous hemicellulose fraction, and a lignin/hydrophobic solvent mixture. The solids can be filtered out for use in the production of other products, while the aqueous hemicellulose fraction and the lignin/hydrophobic solvent mixture can be separated through a simple gravity or decanting separation process, greatly reducing the need for energy-intensive distillation.

According to another aspect of the present invention, the cellulose output from the organosolv process can be utilized in multiple applications, such as in a paper production process as well as in a saccharification process to produce additional amounts of the solvent utilized in the organosolv process to make the overall process self-sustaining. The saccharification process employs a pretreatment step of binding cellulose enzymes to the cellulose to depolymerize the cellulose into smaller strands that enables the saccharification process to more easily and efficiently produce the solvent.

According to still another aspect of the present invention, the lignin/solvent biofuel mixture obtained from the organosolv process may find use directly and independently as a fuel, or can be blended with biodiesel to improve the energy density and gelling temperature of the biodiesel. The lignin/solvent biofuel produced can be utilized as a suitable replacement for diesel or aviation fuel as a result of the high energy density of the lignin/solvent biofuel.

According to still a further aspect of the present invention, the process for producing the lignin/solvent biofuel can be integrated into pulping plants that can be configured to flexibly produce lignin-solvent, pulp and solvent, changing the particular output according to market demand.

Numerous other aspects, features and advantages of the present invention will be made apparent from the following detailed description taken together with the drawing figure.

BRIEF DESCRIPTION OF THE DRAWINGS

The drawing figures illustrate the best mode contemplated of practicing the present invention.

In the drawings.

DETAILED DESCRIPTION OF THE INVENTION

Figure 1:
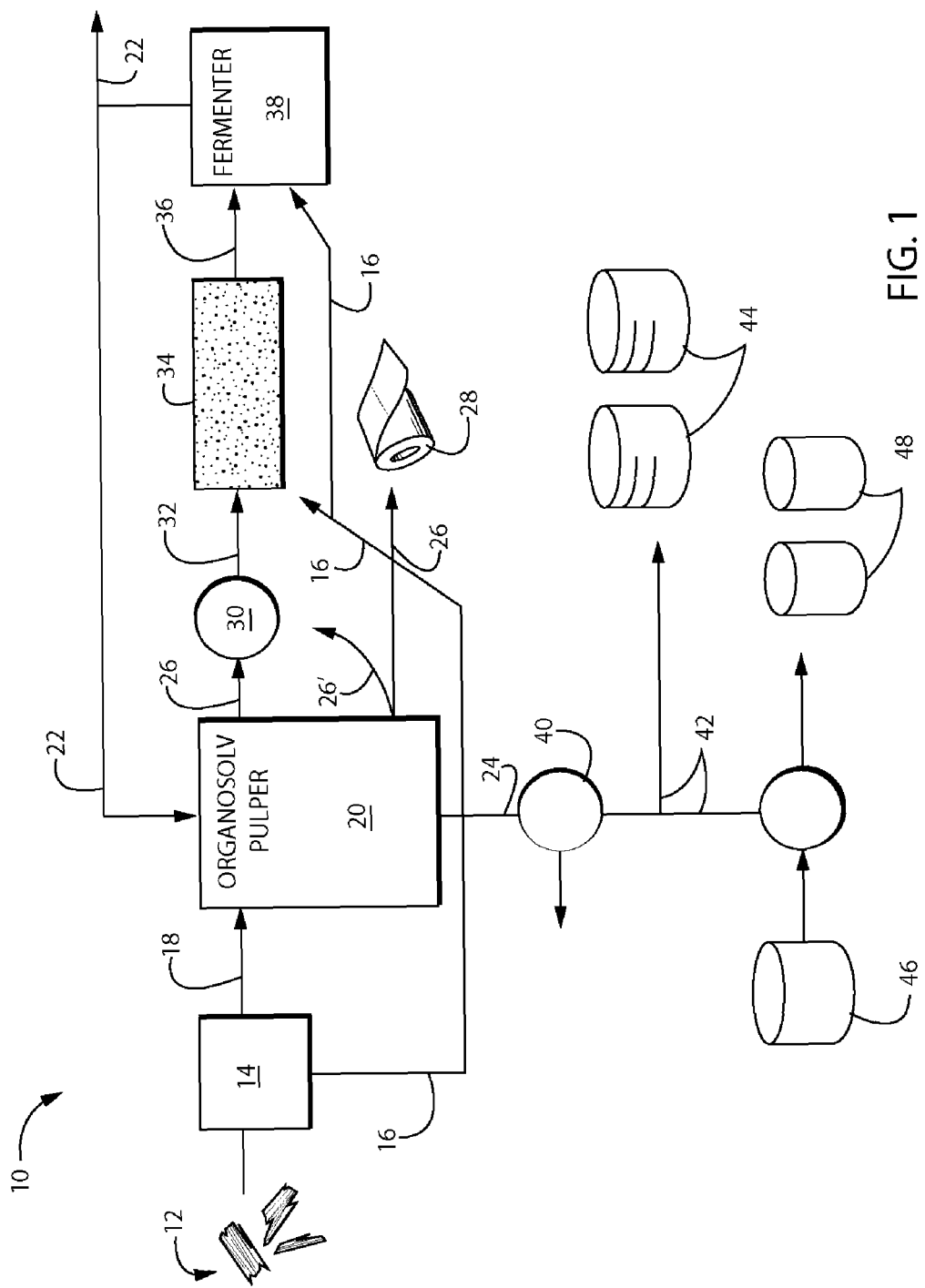
FIG. 1 is a schematic representation of a first embodiment of a biorefinery plant for producing a lignin-solvent fuel constructed according to the present invention.
Figure 3:
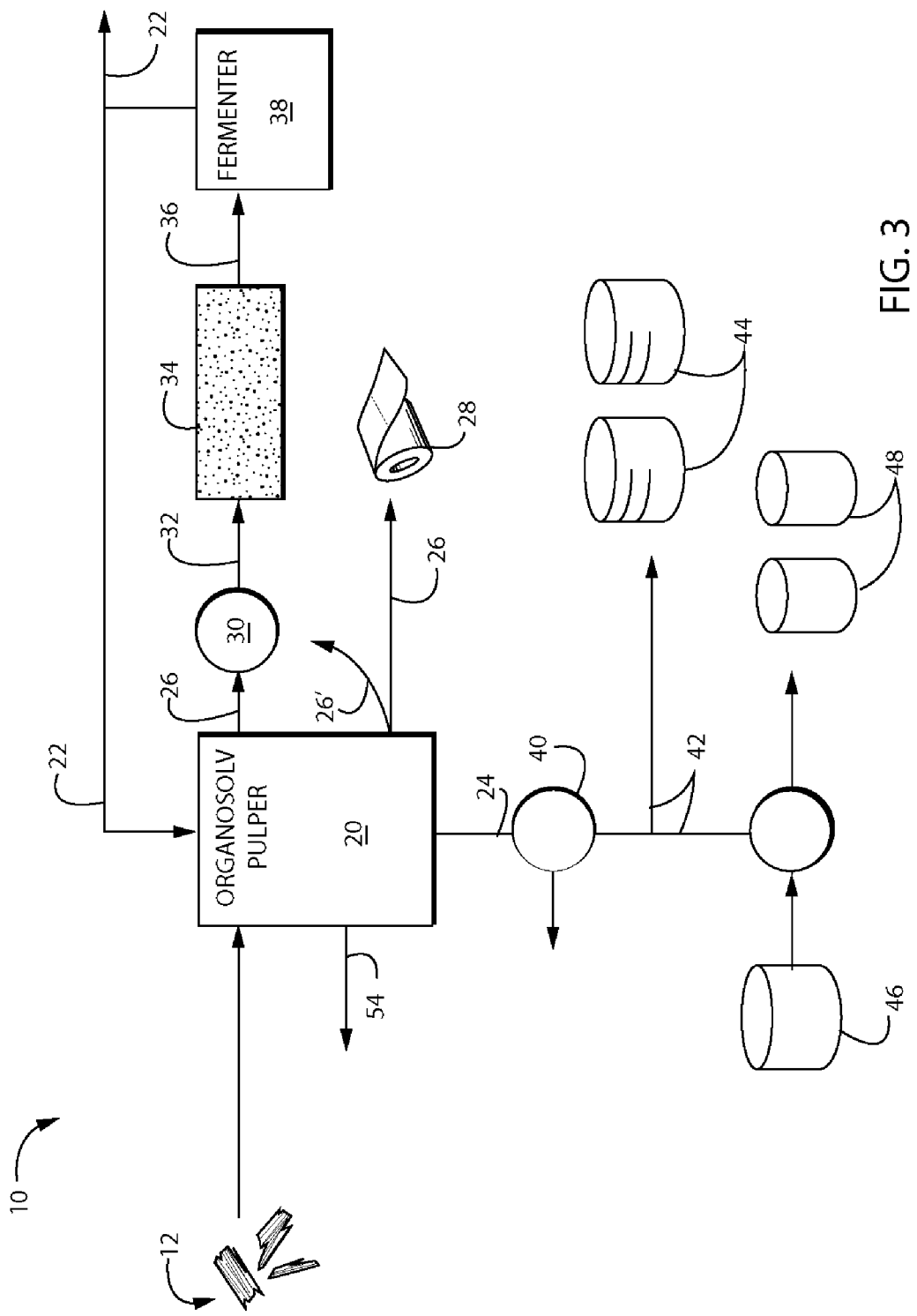
FIG. 3 is a schematic representation of a third embodiment of a biorefinery plant for producing a lignin-solvent fuel constructed according to the present invention.
Figure 4:
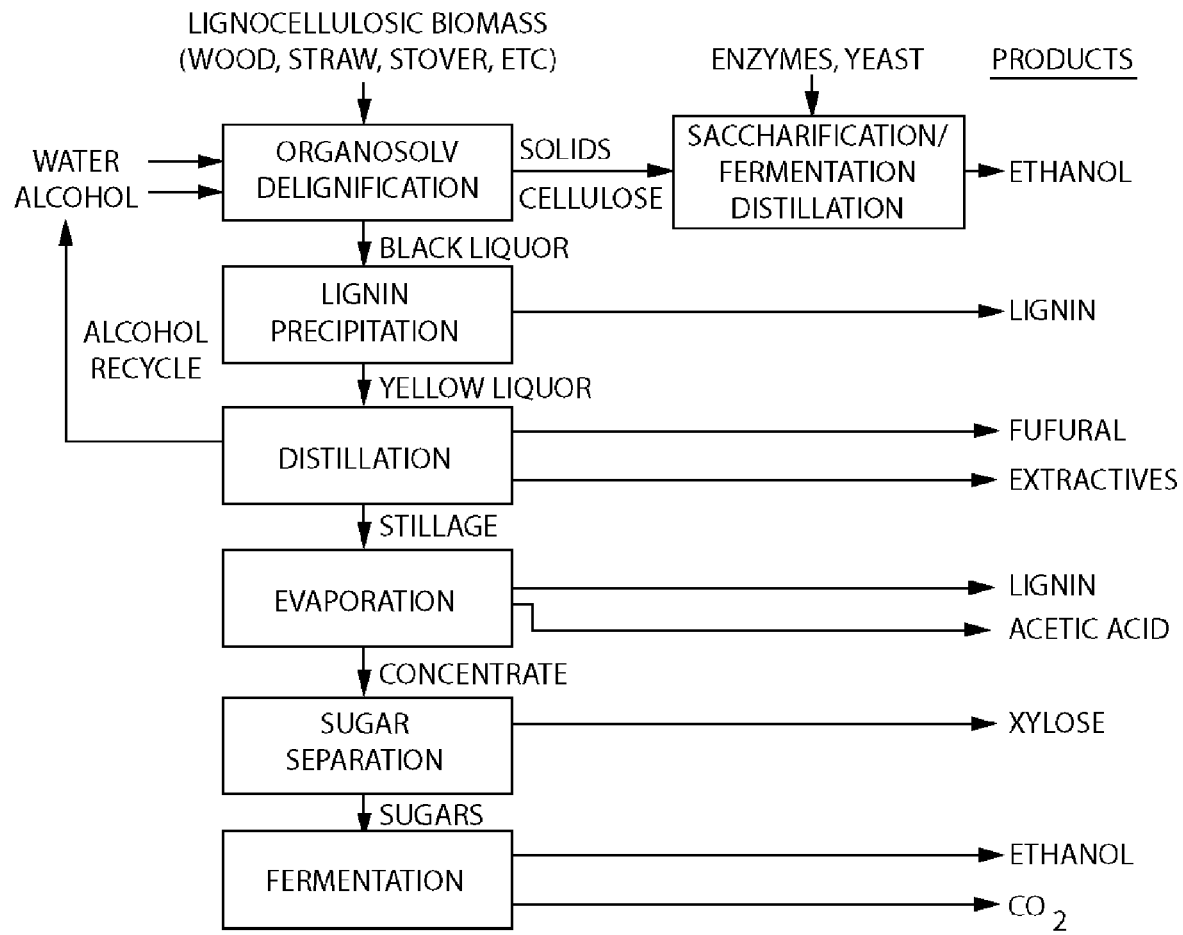
FIG. 4 is a schematic representation of a prior art organosolv biorefinery process.

Referring now to the drawing figures in which like reference numerals designate like numerals throughout the disclosure, FIG. 1, a lignin-solvent biorefinery 10 is illustrated that can accept any kind of lignocellulosic biomass or plant fiber 12, for example, from hardwood or softwood trees, bioenergy crops such as Miscanthus or switch grass, agricultural refuse such as sugar cane, corn stover, or wheat straw, and from other sources such as flax, jute, switch grass, and kenaf, among others. These cellulose plant fiber materials 12 may be chipped, chopped and/or ground to an appropriate size and received by a pre-treater 14 to remove hemicellulose 16 from the biomass or plant fiber 12 according to techniques well known in the art for use with various types of plant fiber 12, such as by utilizing steam or dilute acid. Hemicelluloses are easy to remove via the pre-treater 14 and their absence will simplify the rest of the process and eliminate the complicated downstream separation of hemicellulose and cellulose sugars. As shown in FIG. 3, in one embodiment for the biorefinery 10 the hemicellulose 16 can then be taken from the pre-treater 14 as a sugar mixture that can be utilized as a feedstock in other processes, such as a fermentation process 38, to form various products, including alcohols such as n-butanol, and methyl butenol, and isoprene, which can be re-utilized by the biorefinery 10.

The remaining lignocellulosic material 18 is also removed from the pre-treater 14 and received by an organosolv pulper 20 which, for example, can employ the Alcell® process described above. The organosolv pulper 20 receives an organic solvent 22 to extract the lignin from the cellulose of the lignocellulosic material 18, producing a first product stream of a "black liquor" 24 comprised of the aqueous solvent and lignin that is used to form a lignin-solvent mixture 42 in a manner to be described, as well as a second product stream comprising the purified cellulose 26. To produce the purified cellulose 26 and the black liquor 24 product streams, the pulper 20 is operated at conditions most conducive to the separation of the lignin from the cellulose. These conditions may vary based on the particular solvent 22 utilized in the pulper 20, but preferably are a solvent/water concentration range of 30 to 70 percent by weight or volume in water, an acid addition of a suitable acid of 0.1 to 5 percent based on the weight of oven-dry biomass, temperatures of 150 to 250 degrees C., cooking times of 0.5 to 8 hours, and total liquid to biomass ratio of 3-10:1 (total liquid:oven-dry biomass).

The resulting purified cellulose 26 may be employed in a variety of other processes, such as in a conventional papermaking process 28. Thus, the biorefinery 10 can be located near or incorporated into various existing facilities, such as papermills, which are able to utilize the purified cellulosic materials 26 produced by the biorefinery 10.

Alternatively, or in addition to its use in other processes, any portion of the purified cellulose or pulp 26 produced in the organosolv pulper 20 can be provided to a depolymerization treatment 30 together with fines 26' or other cellulose fiber that is generated by the organosolv process in the pulper 20 but is unsuitable for use in other processes, e.g., paper making. The depolymerization treatment 30 pre-treats the cellulose 26 by catalytically attacking the cellulose to reduce its polymer length by contacting the cellulose 26 with a suitable catalyst such as those commercially available from Hydrite of Waukesha, Wis. This step is optional to increase the rate of enzymatic saccharification, as the cellulose pulp 26 produced in the organosolv pulper 20 can also be converted directly to sugars using commercially available cellulase enzymes like those available from Genencor or Novozymes without use of the depolymerization treatment 30.

The organosolv cellulose pulp 26 or pre-treated organosolv cellulose pulp 26 is then received by a saccharification unit 34 in which the saccharification process occurs to break the cellulose strands down into simple sugars, e.g., glucose, which are more easily and efficiently processed. The saccharification conditions utilized in the unit 34 vary based on the cellulose pulp 26 feedstock and preferably include a temperature between 37 and 50 degrees C., an enzyme concentration of 0.1 to 5 percent by volume, and a pH that is maintained according to the enzyme manufacturer specifications using a suitable buffer. Also, as shown in FIG. 1, the hemicellulose 16 previously extracted in the pre-treater 14 may also optionally be introduced into the saccharification unit 34 or the fermenter 38.

Figure 2:
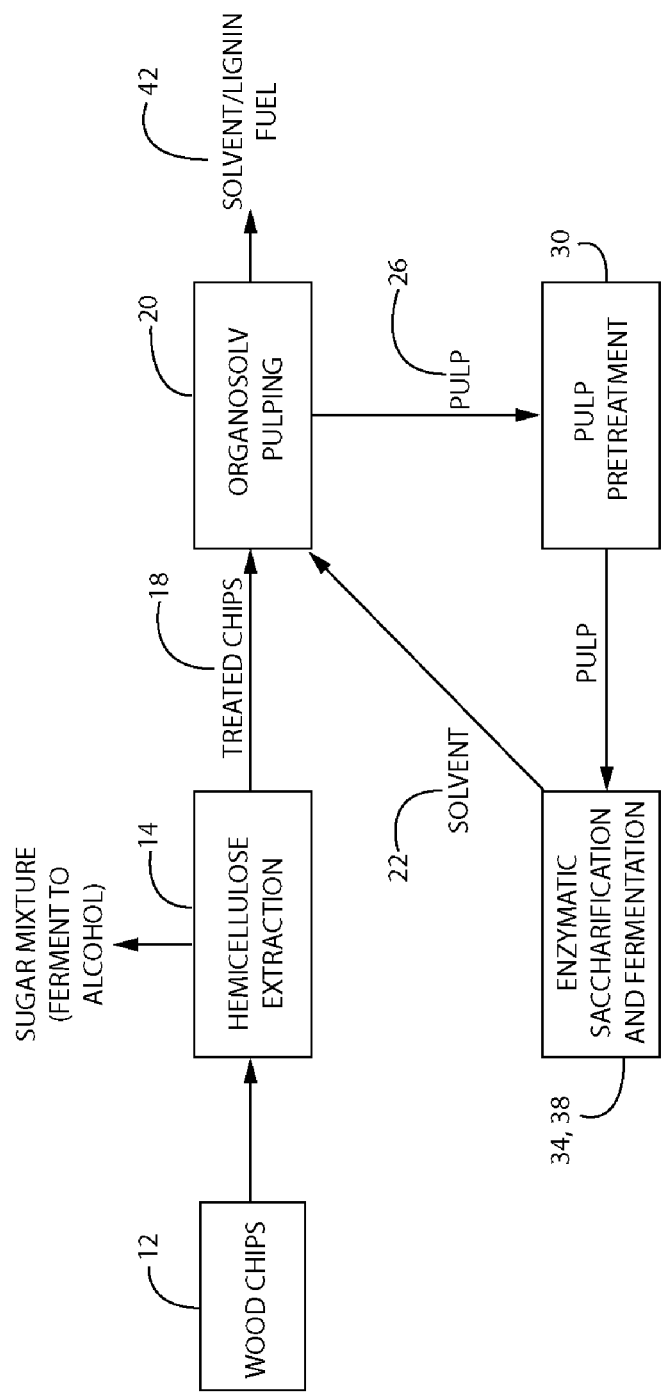
FIG. 2 is a schematic representation of a second embodiment of a biorefinery plant for producing a lignin-solvent fuel constructed according to the present invention.

From the saccharification unit 34, the simple sugars 36 formed therein are sent to a bioreactor or fermenter 38 for reaction with selected yeasts and/or bacteria at specified temperatures and pressures to convert the simple sugars 36 into one or more products. Preferably, the fermenter 38 can have its operating conditions altered as desired in order to enable the fermenter 38 to produce different products from the simple sugars 36 as needed. Alternatively, as shown in FIG. 2, the saccharification step 34 and fermentation step 38 can be combined into one step, or simultaneous saccharification/fermentation by adding the cellulose, cellulase enzymes, and yeast/bacteria in one reaction vessel.

For example, in one embodiment for the biorefinery 10, the fermenter 38 can be operated with genetically modified bacteria at temperatures between 30 and 50 degrees C, and at a pH of 5 to 8 to produce isoprene as a high-value bioproduct from the simple sugars 36. Isoprene ($C_5H_8$) can be polymerized with other organic compounds into rubber, latex, and plastics additives using a variety of catalysts, as is known in the art, and current US industrial consumption of isoprene is primarily for synthesis of cis-polyisoprene (rubber), though it can also be utilized as a chemical feedstock supply as a first step toward fuel production as well as use in the formation of isoprenoid compounds which utilize isoprene as the base compound.

In a particularly preferred embodiment, the fermenter 38 is operated with genetically modified microorganisms that specifically produce n-butanol, or methyl butenol, thereby producing the solvent 22 that can be directed from the fermenter 38 to the pulper 20 for use in the organosolv process, or optionally to other locations for other purposes, such as for use as a biofuel. The solvent 22 produced by the fermenter 38 can be any number of desired alcohols or other compounds capable of being used as the solvent 22, such as ethanol, but preferably is a hydrophobic or water-insoluble solvent, including one or more of the solvents n-butanol and methyl butenol (MBO), as well as mixtures thereof. In one embodiment for the biorefinery 10, MBO is selected as the solvent 22 formed from the simple sugars 36 by the fermenter 38 because MBO is formed from the same biochemical pathway as isoprene gas, such that the changes required to the operating parameters of the fermenter 38 to switch between these respective products are relatively minimal. However, the lignin solvent 22 produced by the fermenter 38 can be used in other processes in addition to its use as the lignin solvent 22.

MBO, and to a slightly lesser extent n-butanol, is also especially preferred for use as the solvent 22 due to its superior benefits in comparison to ethanol because biologically produced 2-methyl-3-buten-2-ol (MBO; $C_5H_{10}O$), is a C5 alcohol with chemical properties more suited to fuel production and use. More specifically, concerning the production of a fuel from the black liquor 24 including the aqueous solvent and the lignin, if ethanol is utilized as the solvent 22, ethanol is miscible with water and not very volatile, and so requires energy-intensive distillation for removal of the water present in the black liquor 24. In contrast, MBO is more volatile and has a density less than that of water, making its separation from water less energy-intensive. Therefore, the water retained in the lignocellulosic material 18 sent to the pulper 20 that is present in the black liquor 24, as well as any water combined with the solvent 22 added to the pulper 20 can be separated using very low energy intensive processes, e.g., by gravity separation, due to the density difference between MBO and water, resulting in a lower energy cost of the separation of the water from the black liquor 24 including MBO lignin solvent and the lignin.

Further, concerning the use of the various solvents 22 as fuel, whereas ethanol ($C_2H_6O$) has an energy density that is about 68% that of gasoline, which lowers fuel mileage and can hinder cold starting of automobiles, the energy density of MBO is about 86% of the energy content of gasoline.

In addition, because ethanol is hygroscopic and hence corrosive, it cannot be transported in pipelines, and damages fuel systems. In contrast, MBO is less corrosive because it is more hydrophobic than ethanol, making its transport and use in fuel systems much easier.

The black liquor 24 produced from the pulper 20 during the organsolv pulping process has any water extracted by passing the black liquor 24 through a decanter or separator 40 to yield the lignin-solvent mixture 42. Due to the use of the n-butanol and/or MBO as the solvent 22, for the reasons stated previously concerning the volatility an density differences between the solvents and water, the removal of the water in the black liquor 24 can be accomplished through simple gravity separation, as opposed to energy-intensive distillation currently required to be used to separate water and ethanol. More specifically, when n-butanol and/or MBO is used as a lignin solvent, the water, being more dense than the solvent, will naturally separate under the influence of gravity from the n-butanol and/or MBO-containing lignin-solvent mixture 42, greatly reducing the energy required for water extraction.

The resultant lignin-solvent mixture 42 will be evaluated as a liquid transportation fuel, and is expected to be a suitable replacement for other fuels. The mixture 42 may be used independently as a fuel 44 or mixed with biodiesel 46 produced by other processes such as those using plant oils, to produce an improved energy density fuel 48 having a lower gelling temperature suitable as a replacement for JP-8 aviation fuel. Furthermore, by retaining the lignin and solvent together in the mixture 42, equipment fouling associated with lignin will be reduced.

In another embodiment of the present invention shown in FIG. 3, the apparatus and method can omit the pre-treater 14, such that the hemicellulose 16 is introduced into the pulper 20 along with the cellulose 26 and the lignin in the form of the biomass of plant fiber 12. As a result of the organosolv process utilized in the pulper 20 with the non-polar, hydrophobic solvent 22, the components introduced into the pulper 20 are formed into three fractions, namely a solid fraction comprised of the cellulose 26, a first liquid fraction 54 comprising an aqueous solution of the hemicellulose 16, and a second liquid fraction comprising the black liquor 24. The cellulose 26 and the black liquor 24 can be processed as described previously, while the hemicelluloses liquid fraction 54 can be converted into other products as well, such the solvent 22.

It should be understood that the invention is not limited in its application to the details of construction and arrangements of the components set forth herein. The invention is capable of other embodiments and of being practiced or carried out in various ways. Variations and modifications of the foregoing are within the scope of the present invention. It also being understood that the invention disclosed and defined herein extends to all alternative combinations of two or more of the individual features mentioned or evident from the text and/or drawings. All of these different combinations constitute various alternative aspects of the present invention. The embodiments described herein explain the best modes known for practicing the invention and will enable others skilled in the art to utilize the invention.

We claim:

1. A biorefinery configured to flexibly process plant fiber materials, the biorefinery comprising:
    a) an organosolv pulper producing purified cellulose and a mixture of lignin and lignin solvent from the plant fiber materials; and
    b) a fermentation system receiving at least a portion of the cellulose, wherein at least one of the pulper or the fermentation system is configured to produce a bio-product, wherein the bio-product is a fuel comprised of the lignin and the lignin solvent exiting the pulper and biodiesel.

2. The biorefinery of claim 1 further comprising a separator for removing water from the mixture of lignin and lignin solvent exiting the pulper.

3. The biorefinery of claim 1 wherein the lignin solvent is selected from the group consisting of: methyl butenol, n-butanol and mixtures thereof.

4. The biorefinery of claim 1 further comprising a pre-treater operable to remove hemicelluloses from the plant fiber materials prior to passing the plant fiber materials to the pulper.

5. The biorefinery of claim 1 wherein the fermentation unit comprises:
    a) a depolymerization treatment unit to reduce the polymer length of the cellulose from the pulper;
    b) a saccharification unit to convert the portion of the cellulose and enzymes from the depolymerization treatment to sugars; and
    c) a fermenter to convert the sugars from the saccharification unit into the bio-product.

6. The biorefinery of claim 5 wherein the bio-product is the lignin solvent.

7. The biorefinery of claim 5 wherein the bio-product is isoprene.

* * * * *